United States Patent [19]

Ryan et al.

[11] Patent Number: 4,801,721

[45] Date of Patent: Jan. 31, 1989

[54] STEREOSPECIFIC SYNTHESIS OF CARBOXYALKYL PEPTIDES

[76] Inventors: James W. Ryan, 3420 Poinciana Ave., Miami, Fla. 33133; Alfred Chung, 8781 SW. 87th St., Miami, Fla. 33173

[21] Appl. No.: 943,798

[22] Filed: Dec. 19, 1986

Related U.S. Application Data

[63] Continuation-in-part of Ser. No. 641,395, Aug. 16, 1984, abandoned.

[51] Int. Cl.$^4$ .................. C07D 209/54; C07D 207/00; C07C 125/06; C07C 101/02; C07C 101/26; C07C 103/19; C07C 103/00; C07C 103/20; C07C 103/07

[52] U.S. Cl. ..................... 548/411; 548/532; 548/533; 548/534; 558/232; 558/242; 560/33; 560/38; 560/41; 560/165; 560/169; 564/152; 564/153; 564/154; 564/157; 564/159

[58] Field of Search ............... 548/411, 532, 533, 534; 558/232, 242; 560/33, 38, 41, 165, 169; 564/152, 153, 154, 157, 159

[56] References Cited

U.S. PATENT DOCUMENTS

| | | | |
|---|---|---|---|
| 3,419,595 | 12/1968 | Hansen ................................. | 558/54 |
| 3,803,199 | 4/1974 | Voss et al. ............................ | 558/46 |
| 3,810,939 | 5/1974 | Ray-Chaudlin ................. | 260/513 R |
| 3,853,939 | 12/1974 | Partos .................................... | 558/56 |
| 4,125,555 | 11/1978 | Reineke ................................ | 558/46 |
| 4,310,461 | 1/1982 | Krapcho et al. ..................... | 548/532 |
| 4,374,829 | 9/1983 | Harris et al. .......................... | 514/21 |
| 4,390,695 | 6/1983 | Krapcho et al. ..................... | 544/130 |
| 4,410,520 | 10/1983 | Watthey ............................... | 548/212 |
| 4,415,496 | 11/1983 | Harris et al. .......................... | 540/521 |
| 4,428,940 | 1/1984 | Markwell ............................. | 514/19 |
| 4,431,644 | 2/1984 | Smith et al. .......................... | 514/222 |
| 4,431,645 | 2/1984 | Smith et al. . | |
| 4,440,759 | 4/1984 | Omura et al. ........................ | 514/30 |
| 4,512,924 | 4/1985 | Attwood et al. ................... | 540/500 |

FOREIGN PATENT DOCUMENTS

| | | |
|---|---|---|
| 1081248 | 7/1980 | Canada . |
| 0073143 | 3/1983 | European Pat. Off. . |
| 0126986 | 4/1984 | European Pat. Off. . |
| 0117448 | 9/1984 | European Pat. Off. . |
| 0134392 | 3/1985 | European Pat. Off. . |
| 3303344 | 2/1983 | Fed. Rep. of Germany . |
| 3317290 | 5/1983 | Fed. Rep. of Germany . |
| 1578224 | 11/1980 | United Kingdom . |

OTHER PUBLICATIONS

Effenberger, V. et al., "Trifluoromethanesulfonate von -Hydroxy-Carbon Sauereestern" Agnew Chem., 95:50 (1983).
Howells, R. D. et al., "Trifluoromethanesulfonic Acid and Derivatives," Chem. Revs. 77(1):69 (1977).
Hansen, R. "Perfluoroalkanesulfonate Esters as Alkylating Agents", J. Org. Chem. 30:4322 (1965).
Burdon, J. et al., "Trifluoromethanesulfonate Esters and Their Alkylating Properties", Tetrahedron 21:1 (1965).
Kato, T. et al., Tetrahedron Letters 48:4741 (1978).
Schroder et al., The Peptides, vol. 1 (Academic Press), p. 181 (1965).
Merrifield, R. B., Advanced Enzymology "Solid Phase Peptide Synthesis", 32:221 (1969).
"Methoden der Organischen Chemie" (Houben-Weyl) vol. XV, part 1, p. 376 (1974).
Ohzeki, M. et al. "Stereochemical Studies", Chem. Pharm. Bull. 25(10):2676 (1977).
Fontana, A., "Selective Removal of Sulphur Protecting Groups of Cysteine Residues by Sulphenyl Halides", J.C.S. Chem. Comm. 976 (1975).
Urbach, H. et al., Tetrahedron Letters 25 (11):1143 (1984).
Hovius, K. et al., "Facile Intermolecular at α-Sulfonyl Carbon", Tetrahedron Letters 24:2477 (1972).
Beard, C. et al., "Synthesis of Some Novel Trifluoromethanesulfonates", J. Org. Chem. 38(21):3673 (1973).
Baldwin, J. et al., "Use of (S)-(Trifloxymethyloxirane in Synthesis", J. Med. Chem. 25(8):931 (1982).
Shiori, T. et al., "Diphenylphosphoxyl Azide", J. Amer. Chem. Soc. 94 (17):6203 (1972).
Katsuhara, Y. et al. "Stereochemistry of the Reaction of Chlorine(I) Trifluoromethanesulfonate", J. Am. Chem. Soc. 101(4):1039 (1979).

Primary Examiner—Delbert R. Phillips

[57] ABSTRACT

Methods for the alkylation of substituted amines with trifluorate esters is disclosed.

4 Claims, No Drawings

STEREOSPECIFIC SYNTHESIS OF CARBOXYALKYL PEPTIDES

This application is a continuation-in-part of application Ser. No. 641,395, filed Aug. 16, 1984, now abandoned.

FIELD OF THE INVENTION

This invention relates to novel methods for the preparation of compounds containing the moiety:

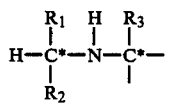  (I)

wherein the chiral carbon atoms shown (C*) are in the L or D configuration, as desired;

$R_2$ is preferably a carboxyl group or a functional derivative thereof, but can also be $CH_2COOH$, $COSH$, $CH_2COSH$, $CH_2SH$, $CH_2CH_2SH$ or a physiologically acceptable, nontoxic salt of any of these, $COOY$, $CH_2COOY$, $COSY$, $CH_2COSY$, $CH_2SY$ or $CH_2CH_2SY$, wherein Y is phenyl, benzyl or an alkyl group having 1–5 carbon atoms, or

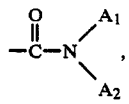

wherein $A_1$ and $A_2$ are the same or different and can be hydrogen, phenyl, benzyl or an alkyl group containing 1–5 carbon atoms, $R_2$ could be any other moiety that preserves the asymmetry of the chiral carbon to which it is attached;

one of $R_1$ and $R_3$ is a complex amido or imido containing moiety of the general formula:

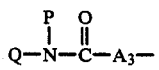  (II)

wherein $A_3$ is:

I. alkylene having 1–6 carbon atoms, branched chain alkyl having 1–6 carbon atoms, cycloalkyalkylene, alkylcycloalkylalkylene, or alkylcycloalkylene;

II. aralkylene, wherein the alkyl group has 1–6 carbon atoms, or alkylaryl;

III. phenyl;

IV. alkylaralkylene wherein the alkyl groups may be the same or different and are 1–6 carbons in length;

V. substituted alkylene, substituted branched chain alkyl, substituted cycloalkylalkylene, substituted alkyl cycloalkylalkylene, substituted alkylcycloalkylene, substituted alkylaryl, substituted aralkylene, substituted phenyl or substituted alkylaralkylene wherein the substituent or substituents may be the same or different, may be included in an alkylene chain or pendent thereto, and are selected from amino, halo, hydroxy, mercapto, nitro, carboxy, carbamyl, lower alkyl, halomethyl, hydroxymethyl, aminomethyl, dihalomethyl, trihalomethyl, cyano, mercaptomethyl, methoxymethyl, methylthiomethyl, methoxycarbonylmethyl, cyanomethyl, benzyl, acetoxymethyl, allyl, isobutyl, mercaptoalkyl having 2–3 carbon atoms, hydroxyalkyl having 2–3 carbon atoms, acetyl thioethyl, benzamido, acetamido, phthaloylaminoalkylene wherein the alkylene group has 1–4 carbon atoms, α-alkoxycarbonyl isoalkylene wherein the alkyl group has 1–5 carbon atoms and the isoalkylene group has 3–5 carbon atoms, benzoylamino, alkanoylamino having 1–5 carbon atoms, alkylamide having 1–5 carbon atoms, phenylamine, alkylamine having 1–5 carbon atoms, lower alkoxy, aryloxy, lower alkylamino, diloweralkylamino, acylamino, arylamino, guanidino, imidazolyl, indolyl, lower alkylthio, arylthio, carboxyamido and lower carbo alkoxy;

VI. alkylenethio or alkylenethioalkylene having 1–6 carbon atoms, or alkylthioalkylene having 1–6 carbon atoms;

VII. alkyleneoxy or alkyleneoxyalkylene wherein the alkyl groups may be the same or different and have 1–6 carbon atoms;

VIII. alkoxyphenyl or alkoxybenzyl wherein the alkoxy groups have 1–3 carbon atoms, phenoxyphenyl, phenoxybenzyl, benzyloxybenzyl or benzyloxyphenyl or a thioether analog of any of them;

IX.

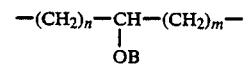

wherein n=0–4, m=0–4, and B=H or a 1–5 carbon atom-containing alkyl group; or an -SB analog thereof;

X.

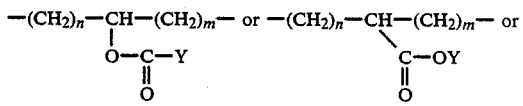

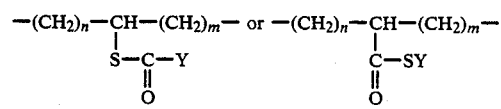

wherein n and m have the same significance as above, Y is phenyl, benzyl or a 1–5 carbon atom-containing alkyl group;

XI.

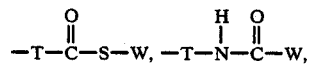

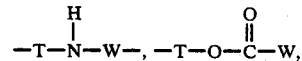

or

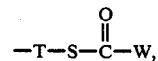

wherein T and W may be the same or different and are alkylene, aryl, benzyl or cycloalkyl; and P and Q may be the same, or one of them may be hydrogen or they may conbine to form a ring with the nitrogen to which they are attached.

Either or both of P and Q may be selected from any of the following:

(a) $C_1$–$C_6$ straight or branched chain alkyl groups or $C_1$–$C_6$ straight or branched chain alkenyl groups, any one of which may be substituted with any of halo, hydroxy, alkoxy, aryloxy, amino, alkylamino, dialkylamino, alkylacylamino, arylamino, guanidino, thioguanidino, nitroguanidino, hydrazino, ureido, nitro, mercaptocarbonyl, hydroxyamino, histidinyl, cyano, imidazolyl, indolyl, mercapto, alkylthio, arylthio, carboxyamido or carboalkoxy, wherein the alkyl groups have 1–6 carbon atoms;

(b) cycloalkyl or cycloalkyl alkylene wherein cycloalkyl has 4–12 carbons and alkylene 1–5 carbons, which may be substituted with any of hydroxy, mercapto, halo, carboxy, thiocarboxy, carbamyl, nitroamine, nitro, methyl, methoxy, carbomethoxy, hydrazino, ureido, thiomethyl, hydroxyamino, cyano, guanidino, thioguanidino or nitroguanidino groups;

(c) aralkyl or alkaryl groups which may be ring substituted with one or more of the following: mercapto, halo, methylenecarboxy, methylenecarbamyl, methylenealkylcarbamyl, thiocarboxy, carboxy, carbamyl, alkylcarbamyl, $CH_2COSH$, mercaptomethylene, hydroxymethylene, hydroxy, nitro, amino, alkyl, alkoxy, aralkyloxy, alkylthio, and aralkylthio groups, wherein the alkyl groups have 1–6 carbon atoms and may also alternatively be chain substituted with methyl, hydroxy, methoxy, halo, thiomethyl,

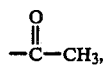

amino, nitro, cyano, mercapto, hydrazino, ureido or hydroxamino, or a thio or nitro derivative thereof, carboxy or thiocarboxy;

(d) an aryl, heterocyclic or adamantanyl group which may be ring-substituted with at least one group selected from halo, hydroxy, oxyalkyl, oxyaryl, amino, alkylamino, dialkylamino, alkylcarbamyl, aminoaryl, guanidino, thioguanidino, nitroguanidino, hydrazino, ureido, nitro, mercaptocarbonyl, hydroxyamino, imidazolyl, indanyl, histidinyl, mercapto, thioalkyl, thioaryl, carbamyl, carboxyalkyl, alkylcarbonyl, carboxyaryl, arylcarbonyl, thiocarboxy, alkylthiocarboxy, arylthiocarboxy and nitro; when P and Q join with N to form a ring, the ring may be any 4–10 membered heterocyclic ring which contains a nitrogen with only two of its valences attached to other ring members.

The other of $R_1$ and $R_3$ may be selected from any of the various groups as hereinafter specified and heretofore defined in U.S. patent application Ser. No. 295,137, filed Aug. 21, 1981 and now abandoned in favor of its copending continuation-in-part Ser. No. 925,232, filed Oct. 31, 1986.

This invention further relates to certain novel trifluoromethanesulfonate ("triflate") ester intermediates produced in the course of carrying out such methods.

BACKGROUND OF THE INVENTION

Methods for the preparation of N-alkylated amines involving the use of triflate esters are known. For example, Effenberger et al, *Angew. Chem.*, 95, 50 (1983) show the use of trifluoromethanesulfonic anhydride to esterify the hydroxyl group in certain α-hydroxycarboxylic acid esters, followed by reaction of the thus-formed triflates with mono- and disubstituted amines (alanine, phenylalanine and aspartic acid are among the specific amines mentioned) to give D- as well as L-N-substituted aminocarboxylic acid esters which, according to the authors, can be hydrolyzed in high yields without demonstrable racemization. Effenberger is also named as an inventor of European published application No. 0134392, published Mar. 20, 1985 which discloses the reaction of compounds of the general formula:

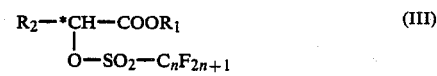

with other compounds

to form end products

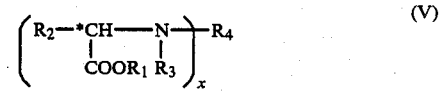

wherein the asterisk denotes an asymmetric carbon, x is 1 or 2, n is an integer of 1 to 6, $R_1$ is a methyl, ethyl or benzyl residue, $R_2$ is a straight or branched chain $C_1$ to $C_8$ alkyl residue which may be unsubstituted or substituted one or more times with any of fluorine, chlorine, bromine, a $C_1$ to $C_8$ alkoxy group, a methoxy-, ethoxy- or benzyloxy-carbonyl group or a phenyl residue that is unsubstituted or substituted with 1, 2 or 3 of the named substituents or alternatively is a phenyl residue that is unsubstituted or has 1–3 of the substituents already named; $R_3$ is H, a straight or branched chain, unsubstituted or singly or multiply substituted $C_1$–$C_{12}$ alkyl residue, an unsubstituted phenyl residue or one that bears 1–3 substituents or an unsubstituted naphthyl residue or one that bears 1–6 substituents, wherein the substituents are selected in each instance from F, Cl, Br, —CN, —OH, $C_1$ to $C_8$ alkoxy, methoxycarbonyl, ethoxycarbonyl, benzyloxycarbonyl, di-$C_1$–$C_8$ alkylamino, an unsubstituted phenyl or one that bears up to 3 substituents or an unsubstituted naphthyl or one that bears up to 6 substituents; when x is 1, $R_4$, independently of $R_3$, may have the same meanings as $R_3$, except for H or may, together with $R_3$ and a nitrogen atom, form a saturated or unsaturated ring of 4–7 atoms containing from 0 to 2 further heteroatoms selected from nitrogen, sulfur and oxyben atoms, which ring is unsubstituted or substituted with any of the substituents named for $R_2$ and $R_3$; when x is 2, $R_4$ is a straight or branched chain 1–12 carbon alkylene residue.

A general discussion of triflates as alkylating agents, including their use in alkylating amines, is found at pages 83 and 84 of a review article entitled "Trifluoromethanesulfonic Acid and Derivatives" by Howells et al, *Chem. Revs.*, 77, No. 1, 69–82 (1977). Hansen, *J. Org. Chem.*, 30, 4322–4 (1965) reported that the reaction of 2,2,2-trifluoroethyl trifluoromethanesulfonate with excess diethylamine in refluxing benzene gave a good yield of the tertiary amine diethyl-2,2,2-trifluoroethylamine. Burden et al, *Tetrahedron*, 21, 1–4 (1965) discuss others' work demonstrating the use of triflates as N-alkylating agents, Watthey, in U.S. Pat. No.

4,410,520, discloses the use of "a lower alkanesulfonic acid, especially methanesulfonic, trifluoromethanesulfonic acid . . ." as an N-alkylating agent in the preparation of 3-amino-[1]benzazepin-2-one-1-alkanoic acids (see column 1, lines 33–46), and Kato et al, *Tetrahedron Letters*, No. 48, 4741-4 (1978) show the N-alkylation of puromycin aminonucleoside with L-3-phenyl-2-phthalimide-1-propanol triflate to give the corresponding N-phthaloyl derivative.

In addition, Hoechst published European patent applications Nos. 0117448, published Sept. 5, 1984 and 0126986, published Dec. 5, 1984 and the U.S. counterpart of the latter, U.S. Pat. No. 4,525,301, issued Sept. 5, 1985 on an application filed Apr. 26, 1984 describe the use of triflate intermediates in various syntheses. More particularly, European application 0117448 describes making compounds

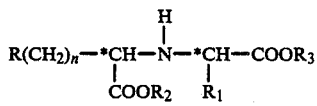
(VI)

either by reacting

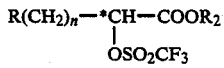
(VII)

with

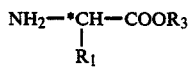
(VIII)

or by reacting

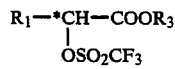
(IX)

with

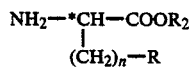
(X)

wherein all asterisks denote asymmetric centers and R, $R_1$, $R_2$, $R_3$ and n are as defined therein. European application 0126986 and its counterpart, U.S. Pat. No. 4,525,301 teach the synthesis of compounds

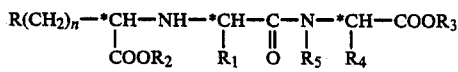
(XI)

by either reacting

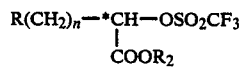
(XII)

with

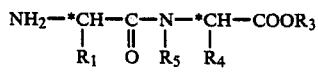
(XIII)

or else by reacting

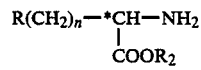
(XIV)

with

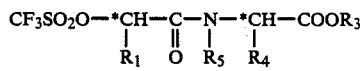
(XV)

wherein all asterisks denote asymmetric centers and R, $R_1$, $R_2$, $R_3$, $R_4$ and $R_5$ are defined therein.

These Hoechst applications do not, however, disclose the preparation of compounds wherein at least one of the moieties corresponding to $R(CH_2)_n$ and $R_1$ of formulae VI to XV, above, is the group

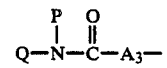
(II)

wherein Q, P and $A_3$ have the meanings given at pp. 2-5 hereof, supra.

DETAILED DESCRIPTION OF THE INVENTION

The present invention rests upon applicant' discovery that triflate intermediates containing the

group (II) on the same asymmetric carbon atom are not stable with the result that the syntheses of compounds containing the moiety of formula (I) above cannot proceed through steps that would necessitate the presence of such an intermediate at any stage.

Thus, one might expect from the Hoechst and Effenberger disclosures that

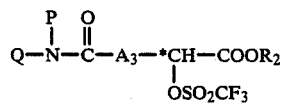
(XVI)

could analogously to Formulae VII and XII above, be prepared and used to synthesize further compounds, or that

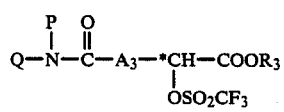
(XVII)

analogous to Formulae IX and XIV above, could be prepared and used in further syntheses. Applicant's finding is that, compounds of Formulae XVI and XVII are unstable and unusable in further practical syntheses.

Applicants' invention is herein illustrated by reference to the preparation of N α-(1-carbethoxy-3-carboanilido propyl)-L-alanyl-L proline, a compound disclosed and claimed in copending application U.S. Ser. No. 295,137, filed by applicants on Aug. 21, 1981. In this compound,

is the specific group

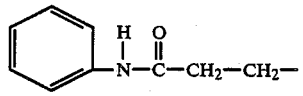

and it appears in the $R_1$ position of Formula I. Applicants have found that the named compound can be synthesized by one of the following schemes:

A.

Step One: 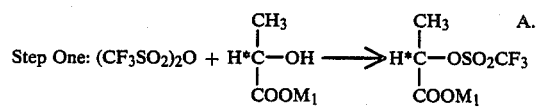

Step Two: 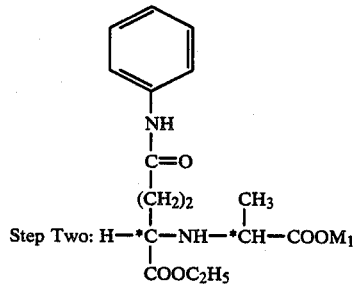

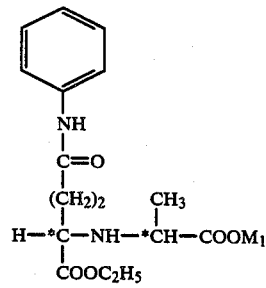

This compound is subjected to routine removal of $M_1$ by methods well known in the art (e.g. hydrogenolysis where $M_1$=benzyl) and subjected to:

Step Three: 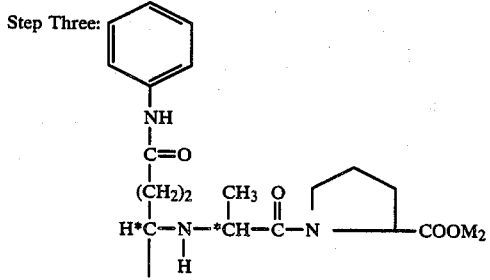

In a variation of this synthesis scheme wherein the

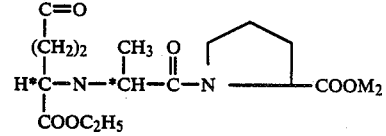

moiety corresponds to $R_3$ of Formula I, wherein the same illustrative substituents are utilized, Step one will involve preparation of

which in Step two will be reacted with

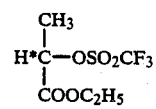

to yield,

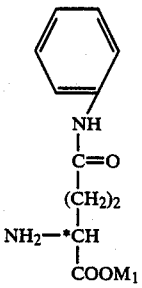

which in turn, after conventional removal of $M_1$, is reacted with protected proline

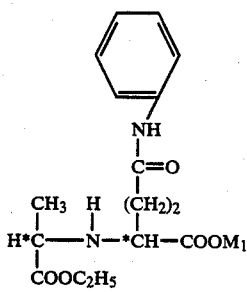

to obtain the desired compound.

Step 1

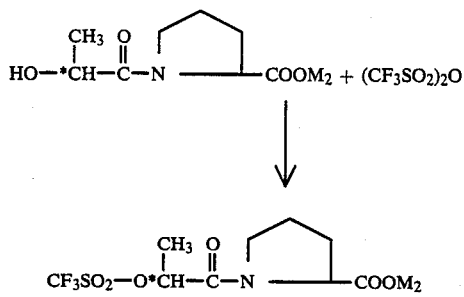

Step Two

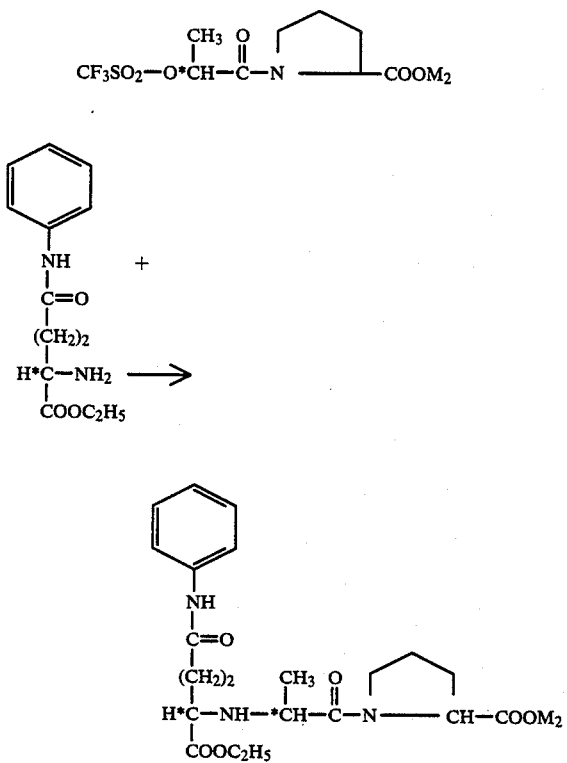

Scheme B is less preferred than Scheme A and applies only to the synthesis of compounds wherein

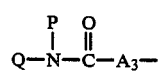

is in the $R_1$ position of Formula I.

Step 1

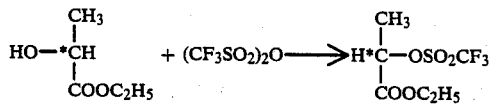

Step 2

B.

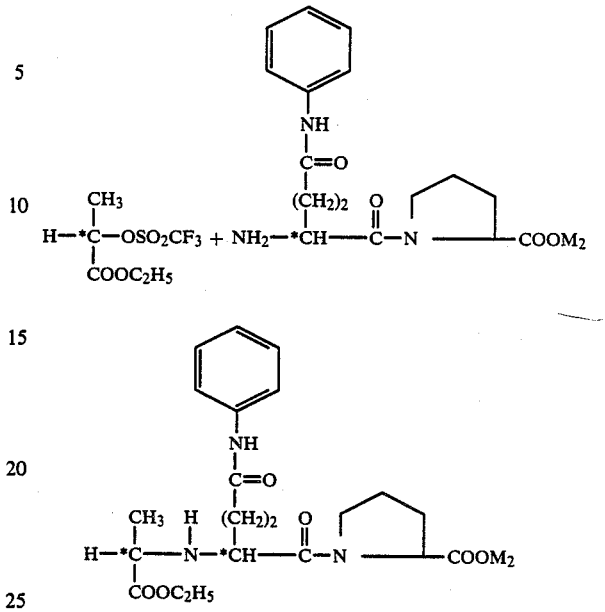

Scheme C applies only to the synthesis of compounds in which $R_3$ of Formula I is

It, too, is less preferred than Scheme A.

In the formulas given in each of the above illustrated reaction schemes, $M_1$ and $M_2$ can represent carboxyl protecting or blocking groups, including ester groups such as benzyl, t-butyl and the like, removable under conditions in which an ethyl ester is stable, and these and any other such groups customarily used in peptide syntheses, e.g., amino protecting groups such as the tert-butyloxycarbonyl (Boc) group, can be employed in carrying out the methods of the present invention. See, for example, Schroder et al "The Peptides", Vol. 1 (Academic Press, 1965) at pages 181–207, and Merrifield, *Adv. Enzym.*, 32, 221 (1969).

In the specific illustrations, $M_1$ and $M_2$ will preferably be benzyl or t-butyl ester groups and can be the same or different.

The thus-protected carboxyl groups can be deprotected by conventional means. For example, a t-butyl ester group can be removed by treatment with trifluoroacetic acid (TFA) in anisole. For a review of other deprotecting methods, see "Methoden der Organischen Chemie" (Houben-Weyl), Vol. XV, part I, page 376 et seq. (1974).

Reaction Scheme A above begins with the triflate of a carboxyl-protected D-α-hydroxycarboxylic acid derivative, e.g., lactic acid benzyl ester. By reacting this triflate with α-ethyl-γ-anilido-L-glutamate (prepared, for example, by reacting an amino-protected L-glutamic acid, such as $N^\alpha$-Cbo-L-glutamic acid, with diethyl sulfate in triethylamine and dichloromethane at room temperature for about three days to give $N^\alpha$-Cbo-α-ethyl-L-glutamate, forming the dicyclohexylamine salt of the thus-obtained glutamate by reaction with dicyclohexylamine in ethyl acetate at room temperature overnight, acidifying a suspension of the dicyclohexylamine salt and then reacting the isolated free acid with dicyclohexylcarbodiimide and aniline in dichloromethane, first in a dry ice/ice/acetone bath for one hour, and then at room temperature overnight), $N^\alpha$-[1(L)-carbethoxy-3-carboxanilidopropyl]-L alanine benzyl ester is obtained.

Following hydrogenolysis to give the corresponding deprotected alanine derivative and reaction with a carboxyl-protected proline, e.g., L-proline benzyl ester as described above for reaction Scheme A, $N^\alpha$-[1(L)-carbethoxy-3-carboxanilidopropyl]-L-alanyl-L-proline benzyl ester is obtained. Conventional deprotection by hydrogenolysis and saponification of the resulting ethyl ester can be used to obtain the free carboxy compound.

Reaction Scheme B illustrated above has as its first step the formation of the triflate of D-lactoyl-L-proline ester, e.g., the t-butyl ester (prepared by reacting D-(+)-acetoxypropionyl chloride with L-proline t-butyl ester, followed by saponification with one equivalent of sodium hydroxide in a mixture of water and acetone), followed by the reaction of this triflate with α-ethyl-γ-anilido-L-glutamate to give the carboxyl-protected N-[1(L)-carbethoxy-3-carboxyanilidopropyl]-L-alanyl-L-proline, e.g., N—[1(L)-carbethoxy-3-carboxanilidopropyl]-L-alanyl-L-proline t-butyl ester, deprotectable, as described above, to the 1-carbethoxy-containing compound on the 1-carboxy-containing compound. Specifics of how to conduct the synthesis of Scheme C and the variation of Scheme A will be readily apparent to those of ordinary skill in the art.

Among the compounds which can be prepared by the novel methods of the present invention are complex amido and imido derivatives of certain of the carboxyalkyl peptides such as those disclosed in European Pat. No. 0073143, based on our aforementioned U.S. patent application Ser. No. 295,137.

These compounds are angiotensin converting enzyme inhibitors, and can be represented by the general formula:

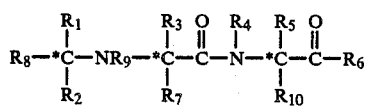

wherein $R_9$ is —H and $R_{10}$ is H, $CH_3$, F, Cl or Br;

$R_2$ is COOH, $CH_2COOH$, COSH, $CH_2COSH$, $CH_2SH$, $CH_2CH_2SH$ or a physiologically acceptable non-toxic salt of any of COOY, $CH_2COOY$, COSY, $CH_2COSY$, $CH_2SY$ or $CH_2CH_2SY$, wherein Y is phenyl, benzyl or an alkyl group having 1–5 carbon atoms; or

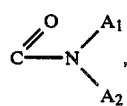

wherein either $A_1$ and $A_2$ may be hydrogen, phenyl, benzyl or an alkyl group having 1–5 carbon atoms;

$R_4$ and $R_5$ together form a ring with the nitrogen and carbon atoms to which they are respectively attached, which ring may be one of the structures:

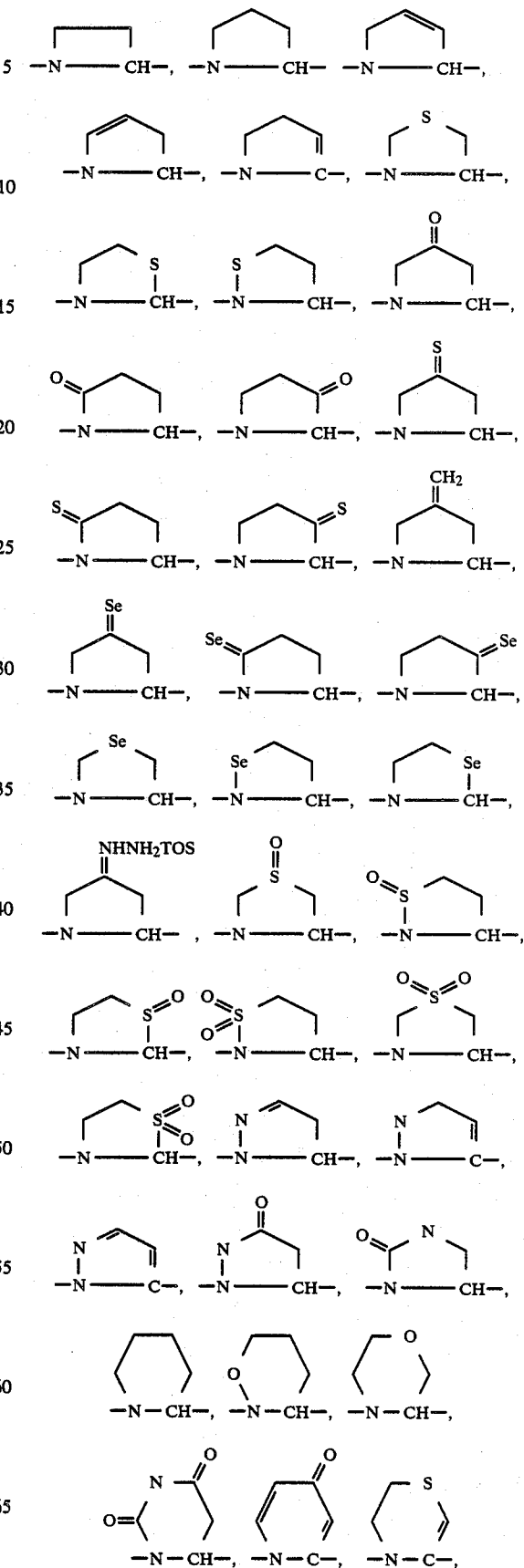

-continued
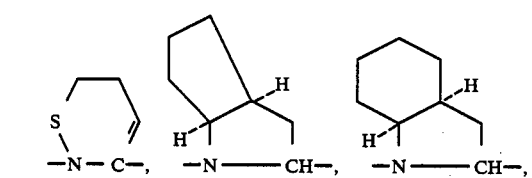
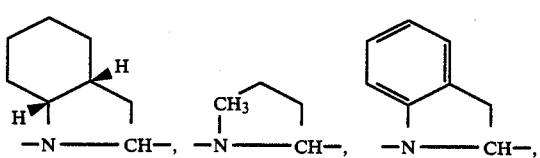
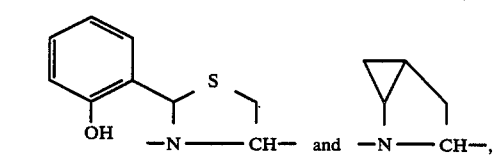
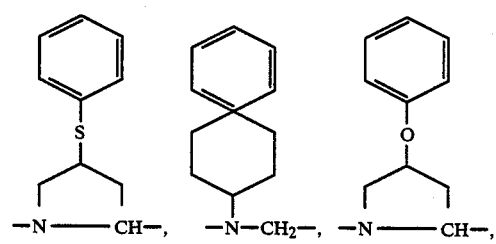
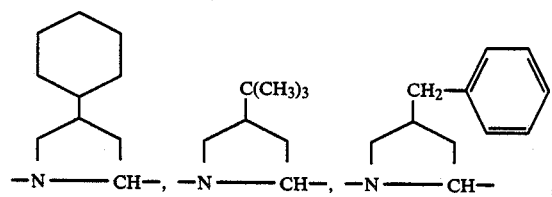
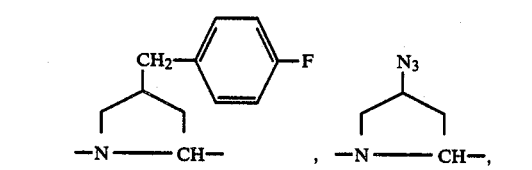
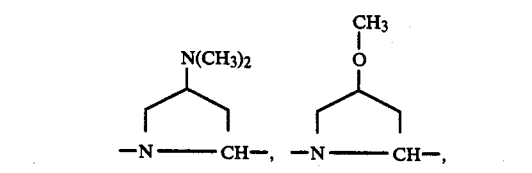
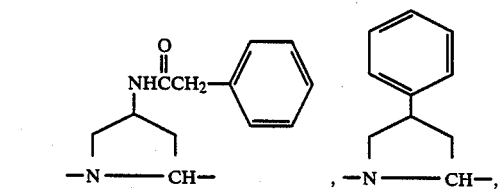
-continued
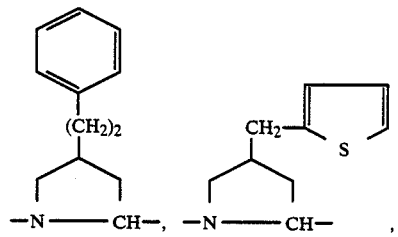
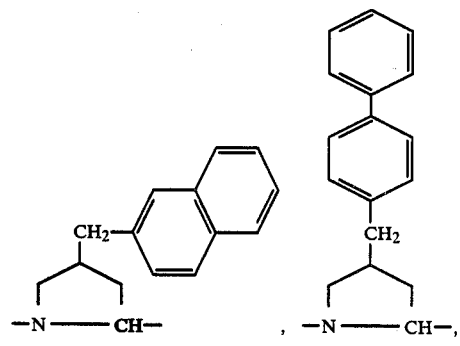
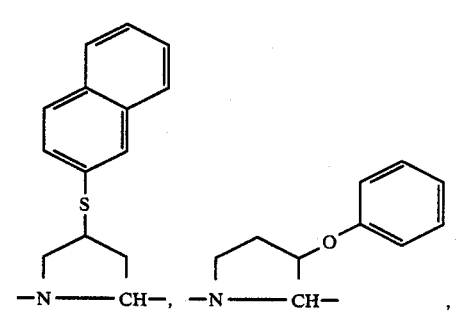
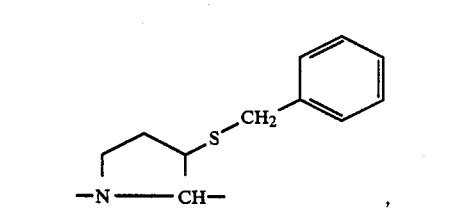
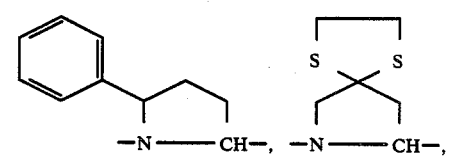
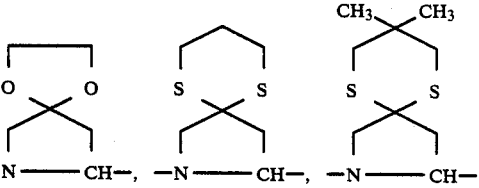
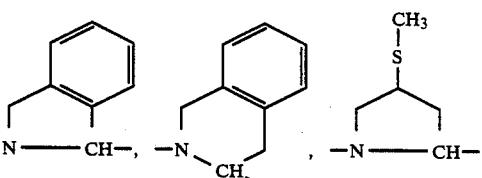

-continued

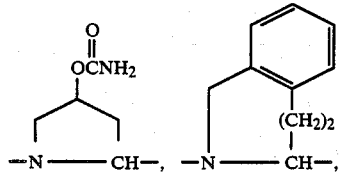

it being understood that any of these structures illustrated as not having such substituents may be monosubstituted with hydroxy, methoxy, halogen (fluoro, chloro, bromo or iodo), phenoxy, benzyloxy,

phenyl, hydroxyphenyl, mercapto, thiomethyl, thiophenyl, thiobenzyl, aminomethyl, methylamino, methyl, hydroxymethyl, propyl, guanidino, nitroguanidino or thioguanidino substituents and that the ring structures may be disubstituted with hydroxy, methoxy or halogen (fluoro, chloro, bromo or iodo), or any combination of two of these substituents, see, for example, U.S. Pat. No. 4,456,761, issued June 26, 1984 to Krapcho at from column 1, line 35 to column 2, line 43, and U.S. Pat. No. 4,456,595, issued June 26, 1984 to Weller et al at column 3, lines 26–60 and column 5, lines 28–63;

$R_6$ is amino, —OM or —SM, wherein M may be hydrogen, an alkyl group having 1–3 carbon atoms or any other ester moiety hydrolyzable under mammalian in vivo conditions to a hydroxyl group, or an ionically bonded anion of a physiologically acceptable non-toxic salt;

$R_7$ is hydrogen, methyl, halomethyl, hydroxymethyl, aminomethyl or mercaptomethyl;

$R_8$ is hydrogen, methyl, amino, halomethyl, hydroxymethyl, aminomethyl, dihalomethyl, trihalomethyl, mercaptomethyl, methoxymethyl, methylthiomethyl, methoxycarbonylmethyl, cyanomethyl, benzyl, acetoxymethyl, allyl, isobutyl, mercaptoalkyl having 2–3 carbon atoms, hydroxyalkyl having 2–3 carbon atoms, ethyl, acetylthioethyl, benzamido, acetamido, phthaloylaminoalkylene wherein the alkylene group has 1–4 carbon atoms, alkoxycarbonyl isoalkylene wherein the alkyl group has 1–6 carbon atoms and the isoalkylene group has 3–5 carbon atoms, benzoylamine, alkanoylamine having 1–6 carbon atoms, alkylamide having 1–6 carbon atoms, phenylamine or alkylamine having 1–6 carbon atoms.

This invention does not apply to complex amido and imido derivatives of carboxyalkyl peptides wherein $R_1$ and $R_3$ are each of the general formula

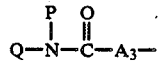

and Q, P and $A_3$ are each as defined above. Such compounds may be synthesized by methods taught in application Ser. No. 295,137.

The invention does apply where $R_1$ is

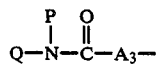

and $R_3$ may be any of, (i) mono-N-substituted alkylamine having 2–4 carbon atoms wherein the N substituent is benzoyl, Boc, Cbo, Tos, formyl or acetyl;

(ii) hydroxyphenyl or hydroxyphenylalkylene having 1–6 carbon atoms or a thiol analog of either;

(iii) mercaptoalkylene having 1–6 carbon atoms;

(iv) phenylalkylene wherein the alkylene group has 1–6 carbon atoms;

(v) phenylthioalkylene or benzylthioalkylene wherein the alkylene group has 1–6 carbon atoms;

(vi) alkylthioalkylene wherein the alkyl and alkylene groups have 1–3 carbon atoms;

(vii) alkoxyphenyl or alkoxybenzyl in which the alkoxy group has 1–3 carbon atoms, phenoxyphenyl, phenoxybenzyl, benzyloxybenzyl or benzyloxyphenyl or a thioether analog of any of them;

(viii)

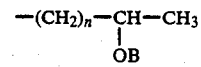

wherein n=0–4 and B=H or a 1–6 carbon atom-containing alkyl group, or an —SB analog thereof;

(ix) —(CH$_2$)$_p$COOZ or (CH$_2$)$_p$COSZ wherein p=0–3 and Z is H, phenyl, benzyl, a 1–5 carbon atom-containing alkyl group, or an anion of a physiologically acceptable salt;

(x)

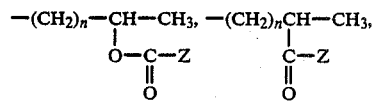

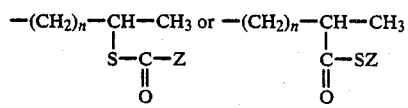

wherein n is 0–4 and Z has the same significance as above;

(xi)

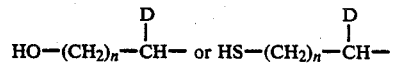

wherein n=0–4, D is phenyl, thienyl or a 1–3 carbon atom-containing alkyl group;

(xii) HO—(CH$_2$)$_n$—C(CH$_3$)$_2$—, HS—(CH$_2$)$_n$—C(CH$_3$)$_2$—, p-hydroxyphenyl—(CH$_2$)$_n$—C(CH$_3$)$_2$— or p-mercaptophenyl—(CH$_2$)$_n$—C(CH$_3$)$_2$— wherein n has the same significance as above;

(xiii) p-mercaptophenyl—(CH$_2$)$_n$—CH$_2$— or p-hydroxyphenyl—(CH$_2$)$_n$—CH$_2$— wherein the phenyl ring has one or two nitro or amino substituents and n has the same significance as above;

(xiv)

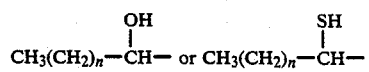

wherein n has the same significance as above;

(xv) aminoalkylene or nitroalkylene containing one hydroxy or mercapto substituent and having 1-6 carbon atoms;

(xvi) hydroxy- or mercaptophenoxybenzyl;

(xvii)

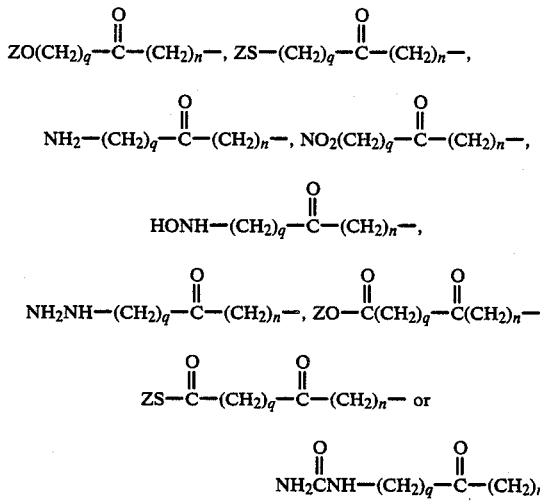

wherein q=1-5 and n is from 0-4 and Z has the same significance as above;

(xviii)

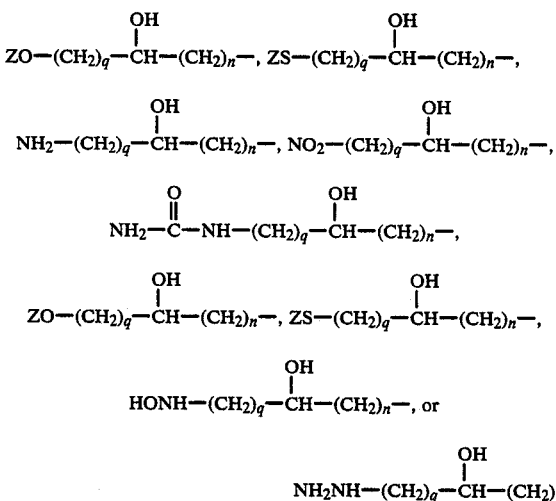

wherein q and n have the same significance as above;

(xix)

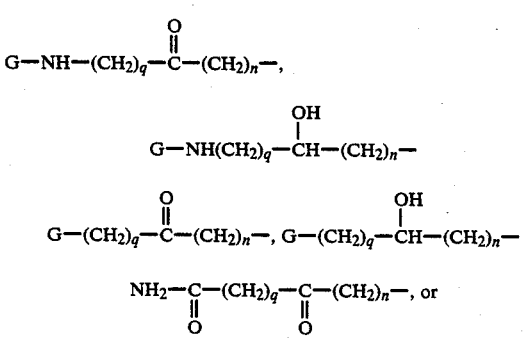

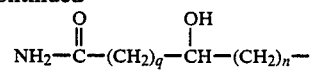

wherein G is an alkacyl or alkacyloxy group having 1-6 carbon atoms, a benzoyl or benzyloxy group, or a phenylalkacyl or phenylalkacyloxy group wherein the alkacyl or alkacyloxy group has 2-6 carbon atoms and q and n have the same significance as set forth above;

(xx)

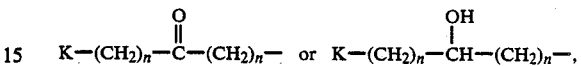

wherein n has the significance stated above and K is selected from carboxyphenyl, aminophenyl, nitrophenyl, halophenyl, hydroxyphenyl, alkylthiophenyl, alkylphenyl, mercaptophenyl, cyanophenyl, mercaptocarbonylphenyl, alkylcarbonylphenyl, alkylcarbonyloxyphenyl, hydrazinophenyl, ureidophenyl, alkylcarbonylaminophenyl, alkylcarbonylthiophenyl, alkyloxyphenyl and hydroxyaminophenyl, wherein all alkyl groups have 1-6 carbon atoms;

(xxi)

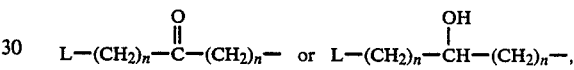

wherein n has the significance stated above and L is selected from cycloalkyl groups having 3-7 carbon atoms which may be unsubstituted or substituted with up to two groups selected from among carboxy, amino, nitro, halo, hydroxy, mercapto, mercaptocarbonyl, hydroxyamino, alkyl, alkylcarbonyl, alkylcarbonyloxy, alkylthio, alkylcarbonylamino, alkylcarbonylthio, cyanohydrazino, ureido and alkyloxy, wherein all alkyl groups have 1-6 carbon atoms;

(xxii) guanidinoalkylene, thioguanidinoalkylene, or nitroguanidinoalkylene in which the alkylene groups have 1-6 carbon atoms;

(xxiii) ring substituted aryl groups in which the ring substituents may be the same or different and may comprise up to five per ring of the following: amino, —OZ, —SZ, halogen, cyano, nitro, —COOZ, —COSZ, carbamyl, hydrazino, alkyl, alkylcarbonyl, alkylcarbonyloxy, alkylcarbonylamino, haloalkyl, dihaloalkyl, trihalomethyl, hydroxyamino, alkylcarbonylthio, phenoxy, and benzyloxy wherein the alkyl groups have 1-6 carbon atoms and Z has the same significance as above;

(xxiv) amidoalkylene or alkylcarbonylaminoalkylene wherein the alkyl and alkylene groups have 1-6 carbon atoms;

(xxv) hydroxyaminoalkylene having 1-6 carbon atoms;

(xxvi) vinyl and substituted vinyl groups in which the substituents may be alkyl, aryl, cycloalkyl or heterocyclic groups;

(xxvii) unsubstituted heterocyclic groups from among phenothiazinyl, pyrrolidinyl, pyrrolyl, quinolinyl, imidazolyl, pyridyl, thyminyl, benzothiazinyl, indolyl, thienyl, purinyl, piperidinyl, morpholinyl, azaindolyl, pyrazinyl, pyrimidyl, piperonyl, piperazinyl, furanyl, thiazolyl and thiazolidinyl, cytosinyl;

(xxviii) alkylene or alkenyl groups having 1-6 carbon atoms substituted with one of the heterocyclic rings from (xxvii) above;

(xxix) groups from (xxvii) or (xxviii) above containing up to four ring substituents on the heterocyclic ring selected from among —OZ, —SZ, —COOZ, nitro, amino, —COSZ, halogen, haloalkyl, dihaloalkyl, trihalomethyl, cyano, carbamyl, alkyl, alkylcarbonyl, alkylcarbonyloxy, alkylcarbonylamino, alkylcarbonylthio, phenoxy, benzyloxy, ureido, hydrazino and hydroxamino, wherein Z has the same significance as above;

(xxx) groups from (xxvii), (xxviii) or (xxix) attached to one valence of an etheric —O— or —S—;

(xxxi) mono-, di- or tri-alkyl-, -alkenyl- or -phenylsilyl or -selenyl wherein the alkyl or alkenyl groups have 1-6 carbon atoms;

(xxxii) any of hydrogen, 1-5 carbon straight or branched chain alkyl, phenyl, hydroxy, alkoxy having 1-6 carbon atoms, benzyloxy, benzyloxyalkylene or phenoxyalkylene wherein the alkylene group has 1-5 carbon atoms, alkoxyalkylene having 1-5 carbon atoms in the alkoxy and alkylene groups, aminoalkylene having 1-6 carbon atoms, alkenyl having 1-6 carbon atoms, benzyl, hydroxyalkyl having 1-6 carbon atoms, mercaptoalkyl having 1-6 carbon atoms, histidinyl, haloalkyl having 1-6 carbon atoms, 4-aminomethylbenzyl, acetamidoalkyl having 1-5 carbon atoms, benzylthiomethylene, or dimethylaminoalkyl having 1-5 carbon atoms.

The present invention also applies where $R_3$ is

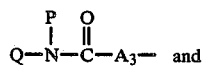 and $R_1$ is any of groups (i)—(xxxii) above, or any of H, $C_1$–$C_8$ straight or branched chain alkyl, phenyl, benzyl, unsubstituted aminoalkylene having 2-6 carbon atoms, hydroxyalkylene having 1-6 carbon atoms, hydroxyphenyl, phenoxyalkylene or benzyloxyalkylene wherein the alkylene group has 1-6 carbon atoms, cycloalkyl having 3-6 carbon atoms, cycloalkyl methyl, 3-indolyl, phenylethyl, methylthioethyl, 3-indolyl alkyl wherein the alkyl group has 1-5 carbon atoms, imidazolyl, imidazolylalkyl wherein the alkyl group has 1-5 carbon atoms, phenoxymethyl, phenylthiomethyl, 4-aminomethylbenzyl, 2-aminophenethyl, naphthylethyl, 4-halophenethyl, 3,4-dihalophenethyl or phenoxyphenethyl.

As will be understood by those of ordinary skill in the art, the novel methods of the present invention can also be used to prepare any compounds wherein the presence of moiety (I),

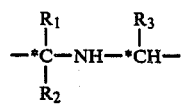

is desired and one of $R_1$ and $R_3$ represents

 (Formula II)

In order that those skilled in the art can more fully understand the present invention, the following examples are set forth. These examples are given solely for purposes of illustration, and should not be considered as expressing limitations unless so set forth in the appended claims.

The thin layer chromatography solvent systems employed in these examples, using silica gel plates (Analtech.), were as follows:

Solvent system 1 [$R_f(1)$] = benzene:acetic acid:water, 9:9:1 parts by volume.

Solvent system 2 [$R_f(2)$] = 1-butanol:acetic acid:water, 75:13:12 parts by volume.

Solvent system 3 [$R_f(3)$] = 1-butanol:pyridine:acetic acid:water, 15:10:3:12 parts by volume.

Solvent system 4 [$R_f(4)$] = chloroform:methanol:ammonium hydroxide, 12:9:4 parts by volume.

Solvent system 5 [$R_f(5)$] = 1-butanol:ethyl acetate:acetic acid:water, 1:1:1:1 parts by volume.

Solvent system 6 [$R_f(6)$] = ethylacetate:pyridine:acetic acid:water, 5:5:1:3 parts by volume.

Solvent system 7 [$R_f(7)$] = ethylacetate:pyridine:acetic acid:water, 200:20:6:11 parts by volume.

Solvent system 8 [$R_f(8)$] = methanol:chloroform, 1:1 parts by volume.

EXAMPLE I

This example illustrates reaction scheme C as set forth above.

1. Preparation of Nα-Cbo-α-Ethyl-L-Glutamate, Dicyclohexylamine salt

Fifty mmol of Nα-Cbo-L-glutamic acid was added in portions to a stirred cold solution of 50 mmol of triethylamine in 30 ml of dry dichloromethane, and the resulting mixture was stirred in an ice bath until a clear solution was obtained. Diethyl sulfate, 55 mmol (obtained by vacuum distillation, 72°–74° C. at about 1 mm Hg) was added, and the resulting mixture was stirred at room temperature for 3 days. Solvent was removed under reduced pressure to yield an oily residue. The residue was taken up in a small volume of ethyl acetate, and washed with dilute cold sulfuric acid and then with a solution of saturated aqueous sodium chloride. The organic phase was dried over magnesium sulfate and filtered, and solvent in the filtrate was reduced to a small volume with a rotary evaporator. The dicyclohexylamine salt was formed by adding 40 mmol of dicyclohexylamine in ethyl acetate. The mixture was left at room temperature overnight, cooled, and the precipitate obtained was collected by filtration. The precipitate was washed with ethyl acetate, then with anhydrous ether, and then dried in a vacuum desiccator over phosphorus pentoxide; yield 9.2 g of white crystals; mp 154.5°–156.5° C. The product was recrystallized in water; yield 6.1 g of white needles; mp 158°–159° C. Infra-red spectrum (CHCl$_3$): zwitterion at 1623 cm$^{-1}$ (strong, sharp) and 1395 cm$^{-1}$ (moderate, broad); carbonyl bands from 1690-1760 cm$^{-1}$ (strong, broad), NH of urethane at 3440 cm$^{-1}$ (weak, sharp).

Thin layer chromatography: $R_f(7) = 0.77$; $R_f(1) = 0.79$; $R_f(2) = 0.71$; $R_f(5) = 0.80$.

Optical rotation: $[\alpha]_D^{25} = -11.0°$ (C=2.5, methanol)

2. Preparation of Nα-Cbo-α-Ethyl-γ-Anilido-L-Glutamate

A suspension of 30 mmol of Nα-Cbo-α-ethyl-L-glutamate dicyclohexylamine salt in 40 ml of water at 0° C. was acidified to pH 2 with a cold, 5% solution of potassium sulfate and potassium hydrogen sulfate (2:1 by weight). The mixture was extracted 3 times with 40 ml of ethyl acetate, and the combined organic phases were then washed 3 times with 3 ml of cold water and 3 times with 5 ml of saturated aqueous sodium chloride solution and the solvent removed under reduced pressure to yield 9.5 g of a clear oily residue.

To a stirred solution of this oily residue in 15 ml of dichloromethane in a dry ice/ice/acetone bath there was then added dropwise, with stirring, a solution of 30 mmol of dicyclocarbodiimide in 15 ml of dichloromethane. One minute after this addition was completed 35 mmol of freshly distilled aniline in 20 ml of dichloromethane was added dropwise. The reaction mixture was stirred in the dry ice/ice/acetone bath for 1 hour, then in an ice bath for 2 hours and finally at room temperature overnight. A precipitate was removed by filtration and was washed with ethyl acetate and ether. The combined organic phases were cooled and then washed with cold dilute hydrochloric acid, saturated aqueous sodium chloride solution, 1M aqueous sodium bicarbonate and saturated aqueous sodium chloride solution. The organic phase was dried over anhydrous sodium sulfate and filtered, and solvent was removed from the filtrate to yield a gel-like residue. The residue was crystallized from isopropanol and isopropyl ether. The white gel-like crystals obtained were broken up in isopropyl ether, recovered by filtration and washed with isopropyl ether to yield 9.85 g of white powder, mp 96°–98° C. Thin layer chromatography: $R_f(1)=0.74$; $R_f(2)=0.75$; $R_f(5)=0.835$; $R_f(7)=0.87$. Infra-red (CHCl$_3$) spectrum: carbonyl bands from 1660–1750 cm$^{-1}$ (strong, broad); no absorption between 2300–2500 cm$^{-1}$; NH band of anilide at 3325 cm$^{-1}$ (moderate, broad); NH band of urethane at 3432 cm$^{-1}$ (moderately strong, sharp); aromatic at 1605 cm$^{-1}$.

Optical rotation: $[\alpha]_D^{25} = -13.8°$ (C=3, methanol)

3. Preparation of α-Ethyl-γ-Anilido-L-Glutamate 2.2 grams of Nα-Cbo-α-ethyl-γ-anilido-L-glutamate was submitted to hydrogenolysis using 0.75 g of 10% palladium on carbon, 30 ml of tetrahydrofuran and ethyl acetate (1:1 by volume) and hydrogen gas at 25 psi for 2.5 hours to give the corresponding deprotected compound. Thin layer chromatography: $R_f(1)=0.58$; $R_f(2)=0.45$; $R_f(7)=0.20$; $R_f(8)=0.65$.

4. Preparation of N-(1-Carbethoxy-3-Carboanilido-propyl)-L-Alanine

Nα-Cbo-α-ethyl-γ-L-glutamyl anilide, 12.5 mmol, was deprotected by hydrogenolysis using 1 g of 10% palladium on carbon in 40 ml of tetrahydrofuran/ethyl acetate (1:1 by volume) at 20 psi at room temperature for 2 hours. The catalyst was removed by filtration, and solvent was removed in vacuo to yield a clear oily residue. Crystals formed on standing at room temperature overnight.

D-1-benzyloxycarbonylethyl triflate (6.3 mmol) in 26 ml of dichloromethane was added dropwise over a period of 30 minutes at room temperature to a vigorously stirred solution of the above-prepared deprotected product in 26 ml of dichloromethane. Thirty minutes later, a solution (4.1 mmol) of triethylamine in 5 ml of dichloromethane was added dropwise over 5 minutes. The mixture was then stirred for 30 minutes, following which solvent was removed in vacuo at 25° C. A 50 ml mixture of ethyl acetate/ether (1:1 by volume) was added to the residue and was washed 5 times with 5 ml of water and then 3 times with 3 ml of saturated sodium chloride solution. The organic phase was dried over anhydrous sodium sulfate and filtered, and solvent was removed under reduced pressure to yield 3.65 g of a yellow oily residue.

Hydrogenolysis of this oily residue was carried out using 1 g of 10% palladium on carbon in 30 ml of ethanol at 20 psi at room temperature for 2.5 hours. The catalyst was removed by filtration and was washed with ethanol. The volume of the combined filtrates was reduced in vacuo to about 7 ml, and 10 ml of ether were then added. White crystals formed at room temperature and were collected by filtration. The crystals were washed with ethanol/ether (1:1 by volume) and dried in a vacuum desiccator over phosphorus pentoxide to yield 0.9 g of product; mp 137°–137.5° C. Another 0.365 g was obtained from the mother liquor by LH-20 column chromatography; column developed with ethanol.

Optical rotation: $[\alpha]_D^{25} = 12.6°$ (C=1; ethanol)

Elementary analysis for $C_{16}H_{22}N_2O_5$; calc C=59.61; H=6.88; N=8.69; found C=58.11; H=6.71; N=8.41.

Thin layer chromatography: $R_f(1)=0.27$; $R_f(2)=0.39$; $R_f(5)=0.62$; $R_f(7)=0.23$ NMR (CD$_3$)$_2$SO and (CD$_3$COCD$_3$)

A triplet at 1.25 δ (CH$_3$ of ethyl ester) overlapping with a doublet at 1.29 δ (CH$_3$ of Ala) (total of 6H); a multiplet overlapping with acetone at 2.05 δ (CH$_2$ of Glu); a triplet at 2.55 δ (2H, —CH$_2$ of Glu); two sets of multiplets of 3.31 δ (CH of Glu) and 3.39 δ (CH of Ala) (total of 2H); a quartlet at 4.10 δ (2H, CH$_2$ of ethyl ester); a broad singlet at 4.57 δ (2H, NH): a multiplet at 7.04 δ (1H); and apparent triplet at 7.27 δ (2H) and an apparent doublet at 7.68 δ (2H) (aromatic); a broad singlet at 9.51 δ (1H, COOH).

Infra-red spectrum (KBr): Zwitterion at 1597 cm$^{-1}$ (strong, broad); carbonyl of anilide at 1670 cm$^{-1}$ (strong, sharp) and carbonyl of ester bond at 1742 cm$^{-1}$ (strong, sharp).

5. Preparation of N-(L-1-Carbethoxy-3-Carboxanilido-propyl)-L-Alanyl-L-Proline

Diphenylphosphoryl azide (2.685 mmol) in 3 ml of dry dimethylformamide was added slowly to a solution of 2.49 mmol of N-(L-1-carbethoxy-3-carboxanilido-propyl)-L-alanine and 2.73 mmol of L-proline benzyl ester hydrochloride salt in 7.0 ml of dimethylformamide, with stirring, at 0° C. The mixture was stirred at 0° C. for 5 minutes and then 5.15 mmol of triethylamine in 5 ml dimethylformamide was added dropwise over 15 minutes. The mixture was then stirred at 0° C. for 3 hours, then slowly warmed to room temperature and stirred overnight. The solution was concentrated to a small volume in vacuo at 40° C. and then diluted with 8 ml of ethyl acetate. The organic phase was washed with half-saturated aqueous sodium chloride solution, then with saturated aqueous sodium chloride solution, then three times with a saturated aqueous solution of sodium bicarbonate, and finally twice more with saturated aqueous sodium chloride solution. The organic phase was dried over anhydrous sodium sulfate and filtered, and solvent was removed in vacuo to yield 1.55 g of oily residue which solidified on standing at room temperature for 1 hour. Addition of absolute ethanol and ethyl acetate caused the formation of salt crystals, which were removed by filtration.

The filtrate was submitted to hydrogenolysis with 300 mg of 10% palladium on carbon in ethanol at 20 psi at room temperature for 2 hours. Catalyst was removed by filtration and solvent was removed from the filtrate in vacuo. The residue was chromatographed on silica gel (2.6×48 cm column) developed with n-butanol/acetic acid/water (75:13:12 by volume). Fractions of 6.25 ml were collected. Fractions 68–85 were pooled. Solvent was removed with a rotatory evaporator. The residue was diluted with water and then recovered by lyophilization resulting in 0.409 gm of white powder.

The material was further purified using an LH-20 column (2.5×96.5 cm) developed with ethanol. Fractions of 6.0 ml were collected and fractions 35–38 were pooled.

Thin layer chromatography: $R_f(1)=0.52$; $R_f(2)=0.38$; $R_f(3)=0.69$; $R_f(5)=0.58$; $R_f(6)=0.745$. $[\alpha]_D^{25}=-57.25°$ (C=1, ethanol)

EXAMPLE II

This example further illustrates reaction scheme C. Preparation of N-[L-1-Carbethoxy-2(N,N-Diethylcarbamoyl)ethyl]-L-Alanyl-L-Proline A. A solution of 4.37 mmoles of D-1-carbobenzyloxy ethyl triflate in 14 ml of dry dichloromethane was added dropwise over 15 minutes to a solution of β-diethyl-L-asparagine-α-ethyl ester (8.74 mmoles) in 14 ml of dry dichloromethane. The mixture was stirred at room temperature for 2 hours, following which solvent was removed in vacuo. 50 ml of 1:1 by volume mixture of ethyl acetate/ether was added to the oily residue. The resulting organic solution was washed ten times with 4 ml of water, and then three times with small volumes of saturated aqueous sodium chloride solution. The organic phase was dried over magnesium sulfate, collected by filtration and the solvent removed in vacuo; yield 1.42 g of yellow oil. Thin layer chromatography revealed a single spot reactive with chlorine/o-tolidine reagents. The residue was hydrogenated using 0.7 g of 10% palladium on carbon in ethanol and ethyl acetate at 25 psi for 2 hours at room temperature. The catalyst was removed by filtration, and solvent was removed from the filtrate in vacuo. White crystals, 0.303 g, were obtained from ethyl acetate and ether; mp 119.5°–120° C. Another 0.155 g was obtained by column chromatography (2.5×95 cm column) on LH-20 (Pharmacia Fine Chemicals) equilibrated and developed with ethanol (8.1 ml fractions, product in fractions 32–37; mp 120.5°–121° C.).

NMR (CDCl₃): multiplet at 1.20 δ (CH₃ of ethylamido and CH₃ of ethyl ester, a total of 12H); a doublet at 1.42 δ (CH₃ of alanine); multiplet at 2.64 δ (2H; CH₂ of aspartyl side chain); multiplet at 3.29 δ (1H; CH₂ of ethylamide and CH of alanine); a multiplet at 3.63 δ (1H, CH of aspartic acid); quartlet at 4.18 δ (2H; CH₂ of ethyl ester); a singlet at 6.0 δ (2H; NH and COOH).

Optical rotation: $[\alpha]_D^{25}+17.7°$ (C=1, ethanol).

Elemental analysis for $C_{13}H_{24}N_2O_5$, FW 288.349, calc: C 54.15, H 8.39, N 9.71, O 27.74; found: C 53.85, H 8.39, N 9.65.

B. To stirred solution of 2 mmol of N-[L-1-carbethoxy-2-(N,N-diethylcarbamoyl)ethyl]-L-alanine and 2.2 mmol of L-proline benzyl ester hydrochloride in 8 ml of freshly distilled dimethylformamide was added dropwise at 0° C. a solution of 2.2 mmol of diphenylphosphoryl azide in 5 ml of dimethylformamide. The mixture was stirred at 0° C. for 5 minutes and then 4.2 mmol of triethylamine in 6 ml of dimethylformamide at 0° C. was added over a period of 10 minutes. The mixture was stirred at 0° C. for 3 hours and then at room temperature overnight, following which the volume of the reaction mixture was reduced by rotary evaporation. Ethyl acetate, 25 ml, and ether, 10 ml, were then added, and the resulting organic phase was washed twice with half-saturated aqueous sodium chloride solution, then twice with saturated aqueous sodium chloride solution, then three times with 3 ml of 1M sodium bicarbonate solution, and finally twice more with saturated aqueous sodium chloride solution. The organic phase was dried over anhydrous magnesium sulfate and filtered, and solvent was removed from the filtrate in vacuo to yield 0.879 g of yellow oil. The oil was hydrogenated, using 0.43 g of 10% palladium on carbon in ethanol at 20 psi for 2 hours. The catalyst was removed by filtration, and solvent was removed from the filtrate in vacuo; yielding 0.85 g of oily residue. The residue was applied to a column (2.5×95 cm) of LH-20 equilibrated and developed with ethanol, and fractions, 6.1 ml, were collected. Fractions 32–35 were pooled, and solvent was removed in vacuo to yield 0.46 g of a glassy residue. Fractions 31, 36 and 37 were resubmitted to LH-20 chromatography. Fractions 33 and 34 of the second column run were pooled, and solvent was removed to yield a hydroscopic glassy residue.

Optical rotation: $[\alpha]_D^{25}=-74.95°$ (C=1; ethanol). Thin layer chromatography on silica gel plates; [solvent systems 1, 2, 3, 4 and 5 respective $R_f$ values: 0.50, 0.15, 0.565, 0.977, 0.48 and 0.906]. Inhibitory activity in vitro, assayed as described in Example 51 of European patent application No. 82304377.3, Publication No. 0,073,143, published Mar. 2, 1983;

before saponification: $I_{50}=2.3\times10^{-6}M$;
after saponification: $I_{50}=2.6\times10^{-9}M$.

Example III

This example illustrates reaction scheme B as set forth above.

1. Preparation of D-(+)-αAcetoxypropionyl-L-Proline t-Butyl Ester

D-α-acetoxypropionyl chloride (20 mmol), prepared according to M. Ohzeki et al, *Chem. Pharm. Bulletin* 25/10, 2676–2680 (1977), in 5 ml of ethyl acetate, was added dropwise over 20 min. at 0° C. to a vigorously stirred mixture of 21 mmol of L-proline t-butyl ester, 20 mmol sodium bicarbonate, 5 ml of water and 5 ml ethyl acetate. The mixture was stirred at 0° C. for 30 min. more, and then at room temperature for 1.5 hours. Work-up yielded 4.27 g of oily residue. Vacuum distillation with collection of the fraction boiling at 158°–162° C. (at 1 mm Hg) yielded 3.4 g of a clear oil.

IR (CDCl₃): Carbonyl of amide bond at 1656 cm⁻¹ and an ester bond at 1737 cm⁻¹.

$[\alpha]_D^{25}=+30.8°$ C. (c=6, dioxane).

2. Preparation of D-Lactoyl-L-Proline t-Butyl Ester

To an ice-cold solution of D-(+)-2-acetoxy-propionyl-L-proline t-butyl ester (3 mmol) in 0.9 ml of water and 2.7 ml of dioxane was added 3 ml of 1M sodium hydroxide. The solution was stirred for 30 min. at 0° C., acidified with acetic acid, and then extracted four times with 5 ml of ethyl acetate. The combined extracts were washed with saturated sodium chloride solution, dried over magnesium sulfate and filtered. Solvent was removed from the filtrate in vacuo to yield the named compound (0.5 g).

IR (CHCl₃): Carbonyl of amide bond at 1642 cm⁻¹ and carbonyl of t-butyl ester bond at 1736 cm⁻¹.

NMR (CDCl₃): Sharp singlet partially overlapping with a multiplet at 1.2–1.5 δ (total of 12H; CH₃—CH(O) and t-butyl); a broad peak at 2.05 δ (4H; —CH₂—CH₂— of proline); a broad multiplet between 3.3–4.0 δ (3H; OH and —N—CH₂— of proline); broad multiplet between 4.0–4.7 δ (—CH(O)— and —NH—CH—COO of proline).

3. Preparation of N-[(D)-1-Oxo-Prop-2-yl-trifluoromethane sulfonate]-L-Proline t-Butyl Ester D-lactoyl-L-proline t-butyl ester (3.5 mmol) was reacted with 3.675 mmol of pyridine and 3.5 mmol of trifluoromethanesulfonic anhydride in dichloromethane in the manner described in Example II, step 2A hereinabove, yielding 1.77 g of the named compound.

IR (CHCl$_3$): triflate band at 1757 cm$^{-1}$ and carbonyl band of t-butyl ester at 1732 cm$^{-1}$.

4. Preparation of N-[(L)-1-Carbethoxy-2-(N,N-Diethylcarbamoyl)ethyl]-L-Alanyl-L-Proline N-[(D)-1-oxo-prop-2-yl triflate]-L-proline t-butyl ester, 1 mmol, and 2 mmol of 2-ethyl-β-N,N-diethyl-L-asparagine in 5 ml of dichloromethane are reacted at room temperature according to the procedure described in Example II, step A hereinabove. The product is chromatographed using a column of Dowex 50W-X8 (H$^+$ form) equilibrated and eluted with ethanol/water (1:1 by volume), followed by water and then 2% pyridine. Fractions containing the desired product are pooled, and the named compound is recovered by lyophilization.

Example IV

Preparation of N-[(L)-1-Carboethoxy-3-Phenylpropyl]-γ-anilido-L-Glutamyl-L-Proline Preparation of Nα-Boc-Nγ-phenyl-L-Glutamine Benzyl Ester*

A solution of 14.84 mmol of dichlohexylcarbodiimide in 10 ml of dichloromethane is added dropwise at −10° C. into a solution of 14.84 mmol of Nα-Boc-L-glutamic acid-α-benzyl ester in 20 ml of dichloromethane. The solution is stirred for 3 min. at −10° C. and then a solution of freshly distilled aniline (16 mmol in 6 ml of dichloromethane) was added. Stirring at −10° C. is continued for 1 hr., then at 0° C. for 2 hrs. and then at room temperature overnight. The reaction mixture is filtered and the precipitate is washed with ethyl acetate. The filtrates are combined and washed until neutral. The organic phase is dried with anhydrous MgSO$_4$ and recovered by filtration. Solvent is removed by rotary evaporation to yield an oily residue.

Crystallization from isopropanol/isopropyl ether: 4.0 g of white needles, mp 104.5-105.5C.

Thin layer chromatography: respectively, solvent systems 7, 8, 1 and 2; R$_f$ values 0.895, 0.77, 0.87 and 0.78.
*"Boc"=tert. butyloxycarbonyl Preparation of Nγ-phenyl-L-glutamine-α-benzyl ester hydrochloride The product of step 1, above, 1.4 g is deprotected in 3 ml of 4.5M HCl in ethyl acetate (0° C. for 5 min., room temperature for 30 min.). The residue obtained by rotary evaporation is treated with ethyl acetate to obtain 1.28 g of white crystals, mp 152°-3° C. Thin layer chromatography, solvent systems 1, 2, 7 and 8: R$_f$ values 0.58, 0.55, 0.45 and 0.70 respectively.

Preparation of N-[(L)-1-carboethoxy-3-phenylpropyl]-γ-anilido-L-glutamic acid

Nγ-Phenyl-L-glutamine-α-benzyl ester is substituted for α-ethyl ester of γ-L-glutamyl-anilide and D-1-ethoxycarbonyl-3-phenylpropyl triflate is substituted for D-1-benzyloxycarbonylethyl triflate in the procedure of Example I, step 4, to yield N-[(L)-1-carboethoxy-3-phenylpropyl]-γ-anilido-L-glutamic acid.

Preparation of N-[(L)-1-carboethoxy-3-phenylpropyl]-γ-anilido-L-glutamyl-L-proline.

By reacting the product of step 3 with L-proline benzyl ester hydrochloride by the procedure described in Example I, step 5, and then by removing the benzyl ester by hydrogenolysis as also described in Example I, step 5, the named compound is obtained.

EXAMPLE V

Preparation of N-[(L)-1-Carboethoxy-3-Phenylpropyl]-γ-anilido-L-Glutamyl-L-Proline Preparation of Nα-Cbz-γ-anilido-L-glutamic acid-α-methyl ester*

Dicyclohexylcarbodiimide, 15 mmol, in 5 ml of dichloromethane was added dropwise at −5° C. to a solution of 15 mmol of Nα-Cbz-L-glutamic acidα-methyl ester in 10 ml of dichloromethane. The solution was stirred at −5° C. for 2 min. and then a solution of freshly distilled aniline, 16.5 mmol in 2 ml of dichloromethane, was added. The resulting solution was stirred at −5° C. for 1 hr. and then at room temperature overnight. After work-up, the product was crystallized from isopropyl alcohol and isopropyl ether: 4.11 g white crystals; mp 87°-91° C. Thin layer chromatography using solvent systems 1, 2, 7 and 8: respective R$_f$ values, 0.825, 0.76, 0.81, 0.79.
*Cbz=carbobenzyloxy Preparation of Nα-Cbz-γ-anilido-L-glutamic acid The product of the first step above, 9 mmol, was saponified in 9 ml of 1M NaOH plus 9 ml of acetone with stirring for 1 hr. at room temperature. A small precipitate was removed by filtration and was washed with water. The combined filtrates were extracted twice with 2 ml of ethyl acetate. The aqueous solution was chilled and then adjusted with 1M HCl to about pH 2 in the presence of ethyl acetate. The organic phase was washed with saturated NaCl solution, dried over MgSO$_4$ and then collected by filtration. Solvent was removed in vacuuo to yield white crystals. Recrystallization from ethyl acetate: 1.86 g white crystals (needles); mp 158°-9° C. Thin layer chromatography using solvent systems 1, 2, 7 and 8; respective R$_f$ values, 0.79, 0.71, 0.55 and 0.67.

Preparation of Nα-Cbz-γ-anilido-L-glutamyl-L-proline t-butyl ester

Dicyclohexylcarbodiimide, 5 mmol in 3 ml of dichloromethane, is added slowly to a solution of 5 mmol of Nα-Cbz-γ-anilido-L-glutamic acid and 5 mmol of 1-hydroxybenzotriazole in a mixture of 3 ml of dichloromethane and 3 ml of dimethylformamide; all at −5° C. After 2 min. of stirring at −5° C., a solution of 5.5 mmol of L-proline t-butyl ester in 1 ml dichloromethane is added. The mixture is stirred at −5° C. for 1 hour and then at 4° C. overnight. Work-up yields the named compound.

Preparation of γ-anilido-L-glutamyl-L-proline t-butyl ester

Product of the last-above step is treated by hydrogenolysis using 10% Pd on carbon in methanol at 20 psi for 1 hr. to yield the named compound.

Preparation of N-[(L)-1-carboethoxy-3-phenylpropyl]-γ-anilido-L-glutamyl-L-proline The product of the step just described is reacted with D-1-carboethoxy-3-phenylpropyl triflate by the procedure described in Example I, step 4. The t-butyl ester is removed by treatment with anhydrous trifluoroacetic acid in anisole to yield the named compound.

The above discussion and related illustrations of the present invention are directed primarily to preferred embodiments and practices thereof. It will be readily apparent to those skilled in the art, however, that numerous changes and modifications in the actual implementation of the concepts described herein can readily be made without departing from the spirit and scope of the invention as defined by the following claims.

What is claimed is:

1. A process for preparing a compound containing the moiety $$H-\overset{R_1}{\underset{|}{C^*}}-\overset{H}{\underset{|}{N}}-\overset{R_3}{\underset{|}{C^*}}-$$

wherein one of $R_1$ and $R_3$ is of the formula $$Q-\overset{P}{\underset{|}{N}}-\overset{O}{\underset{\|}{C}}-A_3-$$

wherein $A_3$ is:

I. alkylene having 1–6 carbon atoms, branched chain alkyl having 1–6 carbon atoms, cycloalkylalkylene, alkylcycloalkylalkylene, or alkylcycloalkylene;

II. aralkylene, wherein the alkyl group has 1–6 carbon atoms, or alkylaryl;

III. phenyl;

IV. alkylaralkylene wherein the alkyl groups may be the same or different and are 1–6 carbons in length;

V. substituted alkylene, substituted branched chain alkyl, substituted cycloalkylalkylene, substituted alkyl cycloalkylalkylene, substituted alkylcycloalkylene, substituted alkylaryl, substituted aralkylene, substituted phenyl or substituted alkylaralkylene wherein the substituent or substituents may be the same or different, may be included in an alkylene chain or pendent thereto, and are selected from amino, halo, hydroxy, mercapto, nitro, carboxy, carbamyl, lower alkyl, halomethyl, hydroxymethyl, aminomethyl, dihalomethyl, trihalomethyl, cyano, mercaptomethyl, methoxymethyl, methylthiomethyl, methoxycarbonylmethyl, cyanomethyl, benzyl, acetoxymethyl, allyl, isobutyl, mercaptoalkyl having 2–3 carbon atoms, hydroxyalkyl having 2–3 carbon atoms, acetylthioethyl, benzamido, acetamido, phthaloylaminoalkylene wherein the alkylene group has 1–4 carbon atoms, α-alkoxy-carbonyl isoalkylene wherein the alkyl group has 1–5 carbon atoms and the isoalkylene group has 3–5 carbon atoms, benzoylamino, alkanoylamino having 1–5 carbon atoms, alkylamide having 1–5 carbon atoms, phenylamine, alkylamine having 1–5 carbon atoms, lower alkoxy, aryloxy, lower alkylamino, diloweralkylamino, acylamino, arylamino, guanidino, imidazolyl, indolyl, lower alkylthio, arylthio, carboxyamido and lower carbon alkoxy;

VI. alkylenethio or alkylenethioalkylene having 1–6 carbon atoms, or alkylthioalkylene having 1–6 carbon atoms;

VII. alkyleneoxy or alkyleneoxyalkylene wherein the alkyl groups may be the same or different and have 1–6 carbon atoms;

VIII. alkoxyphenyl or alkoxybenzyl wherein the alkoxy groups have 1–3 carbon atoms, phenoxyphenyl, phenoxybenzyl, benzyloxybenzyl or benzyloxyphenyl or a thioether analog of any of them;

IX.

$$-(CH_2)_n-\underset{\underset{OB}{|}}{CH}-(CH_2)_m-$$

wherein n=0–4, m=0–4, and B=H or a 1–5 carbon atom-containing alkyl group; or an —SB analog thereof;

X.

$$-(CH_2)_n-\underset{\underset{\underset{O}{\|}}{\underset{C-Y}{O}}}{CH}-(CH_2)_m- \text{ or } -(CH_2)_n CH-(CH_2)_m- \text{ or}$$
$$\underset{\underset{O}{\|}}{C-OY}$$

$$-(CH_2)_n-\underset{\underset{\underset{O}{\|}}{\underset{C-Y}{S}}}{CH}-(CH_2)_m- \text{ or } -(CH_2)_n-\underset{\underset{\underset{O}{\|}}{C-SY}}{CH}-(CH_2)_m-$$

wherein n and m have the same significance as above, Y is phenyl, benzyl or a 1–5 carbon atom-containing alkyl group;

XI.

$$T-\overset{O}{\underset{\|}{C}}-W-,\ T-\overset{O}{\underset{\|}{C}}-\overset{H}{\underset{|}{N}}-W-,\ -T-\overset{O}{\underset{\|}{C}}-O-W-,$$

$$-T-\overset{O}{\underset{\|}{C}}-S-W,\ -T-\overset{H}{\underset{|}{N}}-\overset{O}{\underset{\|}{C}}-W,$$

$$-T-\overset{H}{\underset{|}{N}}-W-,\ -T-O-\overset{O}{\underset{\|}{C}}-W,$$

or $$-T-S-\overset{O}{\underset{\|}{C}}-W,$$

wherein T and W may be the same or different and are alkylene, aryl, benzyl or cycloalkyl; and P and Q may be identical, straight or branched chain alkyl or alkenyl groups, cycloalkyl or cycloalkyl alkylene groups, aralkyl or alkylaryl groups or heterocyclic, aryl or adamantanyl groups, any of which may be substituted functionally or one of P and Q may be hydrogen and the other a group as aforestated or they may combine to form a ring with the hydrogen to which they are attached; which process comprises the essential steps of:

I. reacting a trifluoromethane sulfonate-yielding reagent with the reactive hydroxyl substituent of a first compound which is free of the group $$Q-\overset{P}{\underset{|}{N}}-\overset{O}{\underset{\|}{C}}-A_3-$$

and contains a chiral carbon atom which bears said reactive hydroxyl substituent; and II. reacting the trifluoromethane sulfonate ester of said first compound obtained in Step I with a second compound containing a chiral carbon atom bearing one

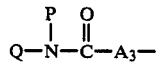

substituent and one primary amino substituent which reacts with said trifluoromethane ester group to form the moiety

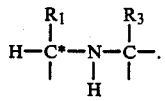

2. A process according to claim 1 in which the said trifluoromethane sulfonate-yielding reagent is trifluoromethane sulfonic anhydride.

3. A process according to claim 1 wherein the end product is of the general formula

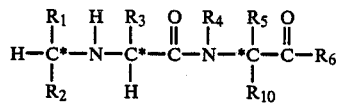

wherein $R_2$ is selected from COOH, $CH_2COOH$, COSH, $CH_2COSH$, $CH_2SH$, $CH_2CH_2SH$ or a physiologically acceptable, nontoxic salt of any of these, COOY, $CH_2COOY$, COSY, $CH_2COSY$, $CH_2SY$ or $CH_2CH_2SY$, wherein Y is phenyl, benzyl or an alkyl group having 1–5 carbon atoms, or

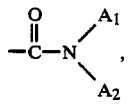

wherein $A_1$ and $A_2$ are the same or different and can be hydrogen, phenyl, benzyl or an alkyl group containing 1–5 carbon atoms; $R_4$ and $R_5$ form a ring with the nitrogen and carbon atoms to which they are attached; $R_6$ is amino, —OM or —SM, wherein M may be hydrogen, an alkyl group having 1–3 carbon atoms or any other ester moiety hydrolyzable under mammalian in vitro conditions to a hydroxyl group, or an ionically bonded anion or a physiologically acceptable non-toxic salt; $R_{10}$ is H, $CH_3$, R, Cl or Br and when $R_1$ is

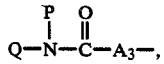

$R_3$ is selected from
(i) mono-N substituted alkylamine having 2–4 carbon atoms wherein the N substituent is benzoyl, Boc, Cbo, Tos, formyl or acetyl;
(ii) hydroxyphenyl or hydroxyphenylalkylene having 1–6 carbon atoms or a thiol analog of either;
(iii) mercaptoalkylene having 1–6 carbon atoms;
(iv) phenylalkylene wherein the alkylene group has 1–6 carbon atoms;
(v) phenylthioalkylene or benzylthioalkylene wherein the alkylene group has 1–6 carbon atoms;
(vi) alkylthioalkylene wherein the alkyl and alkylene groups have 1–3 carbon atoms;
(vii) alkoxyphenyl or alkoxybenzyl in which the alkoxy group has 1–3 carbon atoms, phenoxyphenyl, phenoxybenzyl, benzyloxybenzyl or benzyloxyphenyl or a thioether analog of any of them;
(viii)

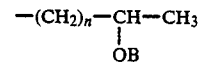

wherein n=0–4 and B=H or a 1–6 carbon atom-containing alkyl group, or an —SB analog thereof;
(ix) —$(CH_2)_p$COOZ or $(CH_2)_p$COSZ wherein p=0–3 and Z is H, phenyl, benzyl, a 1–5 carbon atom-containing alkyl group, or an anion of a physiologically acceptable salt;
(x)

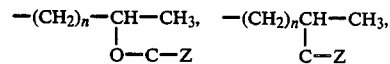

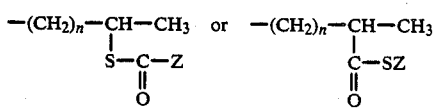

wherein n is 0–4 and Z has the same significance as above;
(xi)

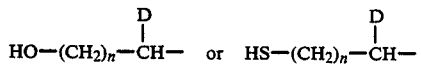

wherein n=0–4, D is phenyl, thienyl or a 1–3 carbon atom-containing alkyl group;
(xii) HO—$(CH_2)_n$—$C(CH_3)_2$—, HS—$(CH_2)_n$—$C(CH_3)_2$—, p-hydroxyphenyl—$(CH_2)_n$—$C(CH_3)_2$— or p-mercaptophenyl—$(CH_2)_n$—$C(CH_3)_2$— wherein n has the same significance as above;
(xiii) p-mercaptophenyl—$(CH_2)_n$—$CH_2$— or p-hydroxyphenyl—$(CH_2)_n$—$CH_2$— wherein the phenyl ring has one or two nitro or amino substituents and n has the same significance as above;
(xiv)

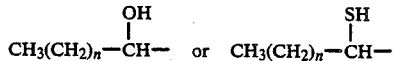

wherein n has the same significance as above;
(xv) aminoalkylene or nitroalkylene containing one hydroxy or mercapto substituent and having 1–6 carbon atoms;
(xvi) hydroxy- or mercaptophenoxybenzyl;
(xvii)

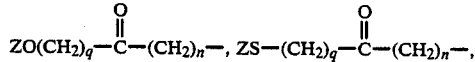

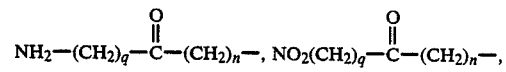

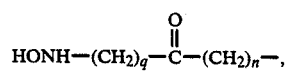

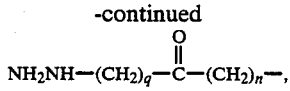

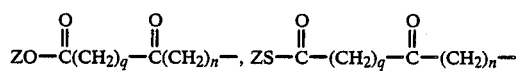

or

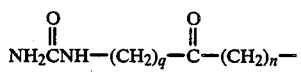

wherein q=1-5 and n is from 0-4 and Z has the same significance as above;

(xviii)

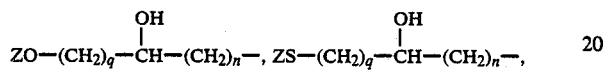

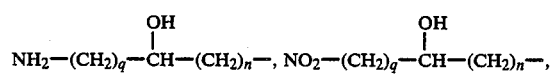

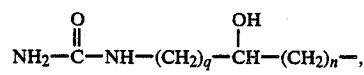

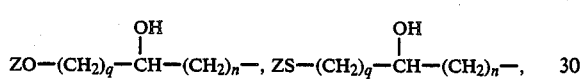

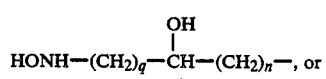

or

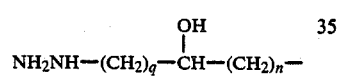

wherein q and n have the same significance as above;

(xix)

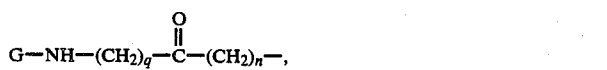

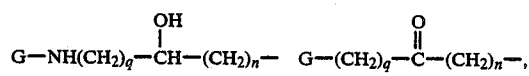

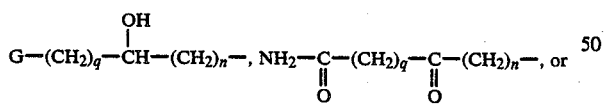

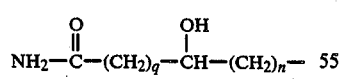

wherein G is an alkacyl or alkacyloxy group having 1-6 carbon atoms, a benzoyl or benzoyloxy group, or a phenylalkacyl or phenylalkacyloxy group wherein the alkacyl or alkacyloxy group has 2-6 carbon atoms and q and n have the same significance as set forth above;

(xx)

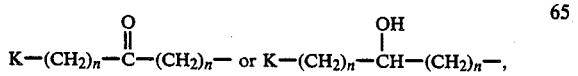

wherein n has the significance stated above and K is selected from carboxyphenyl, aminophenyl, nitrophenyl, halophenyl, hydroxyphenyl, alkylthiophenyl, alkylphenyl, mercaptophenyl, cyanophenyl, mercaptocarbonylphenyl, alkylcarbonylphenyl, alkylcarbonyloxyphenyl, hydrazinophenyl, ureidophenyl, alkylcarbonylaminophenyl, alkylcarbonylthiophenyl, alkloxyphenyl and hydroxyaminophenyl, wherein all alkyl groups have 1-6 atoms;

(xxi)

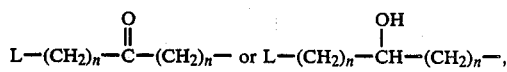

wherein n has the significance stated above and L is selected from cycloalkyl groups having 3-7 carbon atoms which may be unsubstituted or substituted with up to two groups selected from among carboxy, amino, nitro, halo, hydroxy, mercapto, mercaptocarbonyl, hydroxyamino, alkyl, alkylcarbonyl, alkylcarbonyloxy, alkylthio, alkylcarbonylamino, alkylcarbonylthio, cyanohydrazino, ureido and alkyloxy, wherein all alkyl groups have 1-6 carbon atoms;

(xxii) guanidinoalkylene, thioguanidinoalkylene, or nitroguanidinoalkylene in which the alkylene groups have 1-6 carbon atoms;

(xxiii) ring substituted aryl groups in which the ring substituents may be the same or different and may comprise up to five per ring of the following: amino, —OZ, —SZ, halogen, cyano, nitro, —COOZ, —COSZ, carbamyl, hydrazino, alkyl, alkylcarbonyl, alkylcarbonyloxy, alkylcarbonylamino, haloalkyl, dihaloalkyl, trihalomethyl, hydroxyamino, alkylcarbonylthio, phenoxy, and benzyloxy wherein the alkyl groups have 1-6 carbon atoms and Z has the same significance as above;

(xxiv) amidoalkylene or alkylcarbonylaminoallkylene wherein the alkyl and alkylene groups have 1-6 carbon atoms;

(xxv) hydroxyaminoalkylene having 1-6 carbon atoms;

(xxvi) vinyl and substituted vinyl groups in which the substituents may be alky, aryl, cycloalkyl or heterocyclic groups;

(xxvii) unsubstituted heterocyclic groups from among phenothiazinyl, pyrrolidinyl, pyrrolyl, quinolinyl, imidazolyl, pyridyl, thyminyl, benzothiazinyl, indolyl, thienyl, purinyl, piperidinyl, morpholinyl, azaindolyl, pyrazinyl, pyrimidyl, piperonyl, piperazinyl, furanyl, thiazolyl and thiazolidinyl, cytosinyl;

(xxviii) alkylene or alkenyl groups having 1-6 carbon atoms substituted with one of the heterocyclic rings from (xxvii) above;

(xxix) groups from (xxvii) or (xxviii) above containing up to four ring substituents on the heterocyclic ring selected from among —OZ, —SZ, —COOZ, nitro, amino, —COSZ, halogen, haloalkyl, dihaloalkyl, trihalomethyl, cyano, carbamyl, alkyl, alkylcarbonyl, alkylcarbonyloxy, alkylcarbonylamino, alkylcarbonylthio, phenoxy, benzyloxy, ureido, hydrazino and hydroxamino, wherein Z has the same significance as above;

(xxx) groups from (xxvii), (xxviii) or (xxix) attached to one valence of an etheric —O— or —S—;
(xxxi) mono-, di or tri-alkyl-, -alkenyl- or -phenylsilyl or -selenyl wherein the alkyl or alkenyl groups have 1-6 carbon atoms;
(xxxii) any of hydrogen, 1-5 carbon straight or branched chain alkyl, phenyl, hydroxy, alkoxy having 1-6 carbon atoms, benzyloxy, benzyloxyalkylene or phenboxyalkylene wherein the alkylene group has 1-5 carbon atoms, alkoxylakylene having 1-5 carbon atoms in the alkoxy and alkylene groups, aminoalkylene having 1-6 carbon atoms, alkenyl having 1-6 carbon atoms, benzyl, hydroxyalkyl having 1-6 carbon atoms, mercaptoalkyl having 1-6 carbon atoms, histidinyl, haloalkyl 1-6 carbon atoms, 4-aminomethylbenzyl, acetamidoalkyl having 1-5 carbon atoms, benzylthiomethylene, or dimethylaminoalkyl having 1-5 carbon atoms; and when $R_3$ is

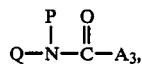

$R_1$ is selected from any of group (i) to (xxxii) above or any of H, $C_1$–$C_8$ straight or branched chain alkyl, phenyl, benzyl, unsubstituted aminoalkylene having 2-6 carbon atoms, hydroxyalkylene having 1-6 carbon atoms, hydroxphenyl, phenoxyalkylene or benzyloxyalkylene wherein the alkylene group has 1-6 carbon atoms, cycloalkyl having 2-6 carbon atoms, cycloalkyl methyl, 3-indolyl, phenylethyl, methylthioethyl, 3-indolyl alkyl wherein the alkyl group has 1-5 carbon atoms, imidazolyl, imidazolylalkyl wherein the alkyl group has 1-5 carbon atoms, phenoxymethyl, phenylthiomethyl, 4-aminomethylbenzyl, 2-aminophenethyl, naphthylethyl, 4-halophenethyl, 3,4-dihalophenethyl or phenoxyphenethyl.

4. In a process for the stereospecific preparation of a compound containing a secondary amino group linked to two chiral carbon atoms via the reaction of a primary amino compound with a trifluoromethane sulfonate ester, the improvement which comprises obtaining an end product in which one chiral carbon atom bears the group

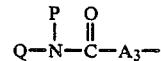

as defined in claim 1 by utilizing a primary amino compound containing said

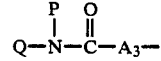

group and a trifluoromethane sulfonate ester that is free of said group.

* * * * *